United States Patent [19]

Alekhin et al.

[11] 4,341,115
[45] Jul. 27, 1982

[54] METHOD AND APPARATUS FOR MONITORING STRUCTURAL AND MECHANICAL PROPERTIES OF DRILLING MUD

[76] Inventors: Stanislav A. Alekhin, Chilanzar, kvartal 24, dom 53, kv. 89; Vitold M. Bakhir, proezd Gaidara, dom 7-a, kv. 17; Raisa I. Born, Chilanzar, kvartal 24, dom 53, kv. 89, all of Tashkent, U.S.S.R.

[21] Appl. No.: 195,423

[22] PCT Filed: Aug. 30, 1979

[86] PCT No.: PCT/SU79/00076
§ 371 Date: May 22, 1980
§ 102(e) Date: Apr. 21, 1980

[87] PCT Pub. No.: WO80/00726
PCT Pub. Date: Apr. 17, 1980

[30] Foreign Application Priority Data

Sep. 22, 1978 [SU] U.S.S.R. .............................. 2665177

[51] Int. Cl.³ ............................................. E21B 47/00
[52] U.S. Cl. .................................................... 73/153
[58] Field of Search .................... 73/153, 59, 61.4; 175/206

[56] References Cited

U.S. PATENT DOCUMENTS 2,266,733 12/1941 Bays et al. ............................... 73/59
3,289,467 12/1966 Parker et al. ......................... 73/61.4

Primary Examiner—Jerry W. Myracle
Attorney, Agent, or Firm—Steinberg & Raskin

[57] ABSTRACT

A method of monitoring structural and mechanical properties of drilling mud and a device for realizing this method includes the determination of the viscosity of drilling mud via a viscosimeter and the determination of the shear strength of the mud via a shear strength measuring instrument, both of which have driven sensitive elements immersed in the drilling mud. The signals of the sensitive elements are converted by converters to indications of the parameters being measured and are compared. The sensitive elements are connected to the same pole of a power source. An electrode immersed in the drilling mud is connected to the opposite pole of the power source. The current flowing between the electrode and the sensitive elements is measured and, when the current is stabilized, the converters produce signals proportional to the viscosity and shear strength of the drilling mid. A first ratio of the shear strength and viscosity signals is determined, the signals being produced by a divider connected to the outputs of the converters. Then, the polarity of the power source is reversed and a second ratio of the shear strength and viscosity signals is determined. The arithmetical mean of the first and second ratios is then determined.

3 Claims, 2 Drawing Figures

METHOD AND APPARATUS FOR MONITORING STRUCTURAL AND MECHANICAL PROPERTIES OF DRILLING MUD

BACKGROUND OF THE INVENTION

1. Field of the Invention

The present invention relates to the preparation and regeneration of drilling mud. More particularly, the invention relates to a method of monitoring structural and mechanical properties of drilling mud and a device for realizing same.

The present invention can be most advantageously used in petroleum and gas industries for preparation of mud.

This invention can also be successsfully employed for regeneration of mud, that is for regeneration of initial properties of mud.

2. Prior Art

At present, clay mud is extensively used in drilling holes of various depths.

Structural and mechanical properties of drilling mud based on clay are often characterized by the viscosity of mud, which is determined by rotary viscosimeters of various designs. Besides, such properties can be characterized by shear strength which can be found by means of laboratory methods.

Structural and mechanical properties of clay drilling mud are currently often defined by the so-called "coagulation index" (CI) which is in fact the ratio of the shear strength to the viscosity of mud. This index characterizes the degree of coagulation of mud.

In modern practice, both characteristics are measured manually and independently, that is, the viscosity is measured by viscosimeters of any type, whereas the shear strength is found by means of a special instrument for measuring the shear strength. Manual measurements are time consuming and irregular, so that accuracy is unavoidably impaired. This, as may be expected, permits no uninterrupted monitoring of mud condition in the process of preparation and during circulation in the hole, which are vital prerequisites of successful hole sinking.

This is also a disadvantage as far as automation of mud preparation is concerned.

SUMMARY OF THE INVENTION

The principal object of the invention is to provide a method and apparatus for monitoring structural and mechanical properties of drilling mud which permit continuous comparison of the values of the shear strength and the viscosity of the drilling mud.

An object of the invention is to provide a method and appartus for the continuous monitoring of the structural and mechanical properties of drilling mud, whose parameters vary fairly frequently, with measurements of high accuracy, thereby providing for better quality and stability of drilling mud.

Another object of the invention is to provide a method and apparatus for the continuous monitoring of the structural and mechanical properties of drilling mud wherein the regeneration of the properties and parameters of mud in the process of circulation is accomplished in considerably less time than in known methods.

The method of monitoring structural and mechanical properties of drilling mud of the invention comprises measurement of the viscosity of the mud by a viscosimeter featuring a driven sensitive element and measurement of the shear strength of the mud via an instrument for measuring the shear strength, having a driven sensitive element. The driven sensitive elements are immersed in the drilling mud in order to obtain figures characterizing each parameter being measured. Later, the figures thus obtained are compared. in accordance with the invention, the sensitive elements are connected to the same pole of the power source. An electrode connected to the opposite pole of this power source is immersed in the drilling mud. Current flowing between the electrode and the sensitive elements is measured. When the current is stabilized, electrical signals are obtained, which are proportional to the viscosity and shear strength of the mud. A first ratio of the shear strength and viscosity signals is determined and then the polarity of the power source poles is reversed and a second ratio of the shear strength and viscosity signals is determined. Then, the arithmetical mean of the first and second ratios is calculated.

It is advisable that the method of the invention be realized by apparatus comprising a viscosimeter having a driven sensitive element immersed in the drilling mud and an instrument for measuring the shear strength, having a driven sensitive element immersed in the drilling mud, both having converters for converting signals supplied from the sensitive elements into signals characterizing, respectively, viscosity and shear strength of the drilling mud. In accordance with the invention, the apparatus comprises a DC power source having one pole connected to the driven sensitive elements of the viscosimeter and the shear strength measuring instrument and another pole connected to an electrode immersed in the drilling mud. The outputs are connected to the inputs of a divider whose output signal is an indicator of the ratio between the shear strength and the viscosity of the drilling mud. The appartus further comprises a polarity reversal switch of the power source, connected at its output, which generates a switch position signal, to an input of a channel switch whose other input is connected to the output of the divider. The two outputs of the channel switch are connected to memories forming two channel for transmission and storage of information fed from the divider, depending on the position of the power source polarity reversal switch. The outputs of the polarity reversal switch are connected to an adder whose output, being the sum of information obtained via the two channels from the divider, is connected to a data output device.

BRIEF DESCRIPTION OF THE DRAWINGS

For a fuller understanding of the invention, reference is had to the following description, taken in connection with the accompanying drawings, wherein.

DESCRIPTION OF PREFERRED EMBODIMENT

For simplicity sake the description starts with basic elements of the apparatus for monitoring structural and mechanical properties of drilling mud.

Practice demonstrates that in the preparation of drilling mud, viscosity and shear strength are by far the most important characteristics of drilling mud. Although persons skilled in drilling understand unambiguously the term "shear strength" (SS), the inventors feel it advisable to stress that they understand the expression as an effort required to disturb the resting mud.

Another parameter, which is the "coagulation index" (CI), has recently been often used to describe the stability of drilling mud. The coagulation index is the ratio of the shear strength to viscosity. It is determined by the relation:

$$CI = (\theta/T) \text{ mg/sm}^2/\text{s},$$

where
$\theta$ shear strength (SS) in a minute, mg/sm$^2$ and
T is the relative viscosity, s.

Figure 1:
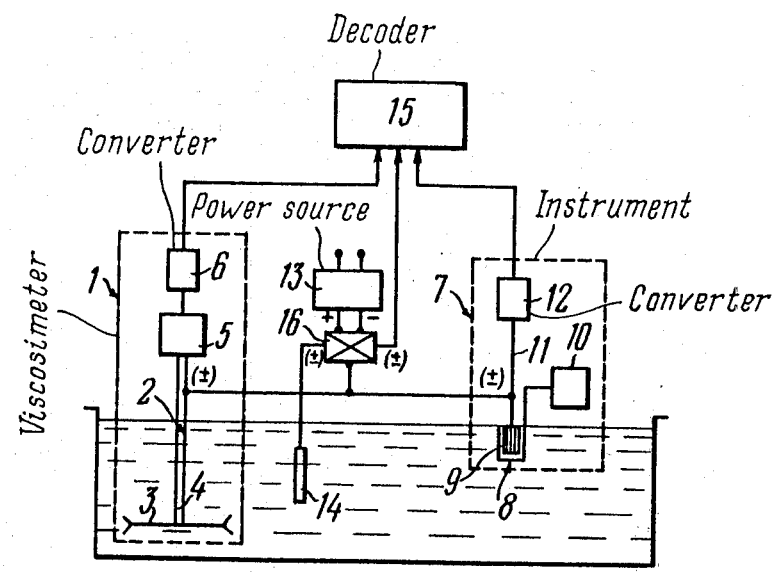
FIG. 1 is a block diagram of an embodiment of the apparatus of the invention for monitoring structural and mechanical properties of drilling mud.

A device for monitoring structural and mechanical properties of drilling mud and, in particular, for monitoring the coagulation index, comprises a viscosimeter 1 (FIG. 1). The viscosimeter may be any of the currently known rotary instruments for measuring the viscosity and capable of providing continuous monitoring of viscosity of drilling mud. In this embodiment, the viscosimeter 1 comprises a sensitive element 2 which is a blade 3 on a shaft 4 connected to an electric motor 5. In order to determine the viscosity of the drilling mud, the blade 3 is immersed in the mud and rotated by the motor 5 and the shaft 4. When the viscosity of the mud changes, by rising, for example, the resistance to the motion of the blade 3 grows proportionally. The shaft 4 thus slows down and changes the current of the motor 5. The change of the current of the motor 5 is, consequently, proportional to the change in the viscosity of the drilling mud. The thus generated signal is supplied from the measuring element 2 to a converter 6.

An instrument 7, which determines the shear strength, is extensively employed in drilling, and comprises a sensitive element 8 made as a ribbed cylinder 9 immersed in a vessel containing drilling mud and driven by a motor 10. The cylinder 9 is connected to a scale via a steel wire 11. The angle of twist of the wire 11 is the source of signals which are transformed by a converter 12 into electric signals proportional, in current, for example, to the shear strength of the drilling mud.

A DC power source 13 and an electrode 14 suitable for immersion in the drilling mud are provided.

There is also a decoder 15 to compare the readings of the viscosimeter 1 and the instrument 7. The sensitive elements 2 and 8, as well as the electrode 14, are connected to the DC power source 13 via a polarity reversal switch 16.

The method of monitoring structural and mechanical properties of drilling mud includes the determination of the viscosity of the mud via the viscosimeter 1 having the sensitive element 2 and the determination of the shear strength of the mud via the shear strength measuring instrument 7 having the sensitive element 8. In the method, the sensitive elements 2 and 8 are coupled to the same pole of the power source 13. The electrode 14 is immersed in the drilling mud 16 and connected to the opposite pole of the power source 13. An electric field is thus produced between the electrode 14 and the sensitive elements 2 and 8. This provides a flow of current in the drilling mud.

If, at the beginning, the polarity of the pole of the power source 13 connected to the sensitive elements 2 and 8 is for example, positive (+), the solid clay particles of the drilling mud, which are charged negatively, would start moving onward towards the positively charged elements. In a while, such particles would bunch around and partly adhere to the surface of the sensitive elements 2 and 8. As the particles bunch around and adhere to the surface of the elements 2 and 8, the current flowing between the electrode 14 and the sensitive elements 2 and 8 is constantly measured.

As more and more particles concentrate about the sensitive elements 2 and 8, the current of the motor 5 grows until the negatively charged particles compensate for the positive charge of the sensitive elements 2 and 8. At such instant, the current is stabilized; that is, it stops growing.

The absolute value of the stabilized current characterizes the maximum viscosity of the drilling mud. The current is in proportion to the viscosity of the mud and the shear strength thereof.

When the current is stabilized, electric signals proportional to the viscosity and shear strength of the drilling mud are obtained. These signals are generated at the outputs of the converters 6 and 12. Thereafter, the first ratio of the shear strength and viscosity signals is determined. Then the polarity of the poles of the power source is reversed. The reversal of polarity results in the sensitive elements 2 and 8 acquiring a negative charge, whereas the electrode 14 is charged positively. The solid negatively charged clay particles are detached from the sensitive elements 2 and 8 and the drilling mud in their zone thins out.

The motors 5 and 10 start rotating with the minimum torque and the current decreases. The second ratio of the shear strength and viscosity is then determined and the arithmetical mean of the first and second ratios is determined therefrom.

The aforedescribed method permits measurement of the viscosity and shear strength at any desired frequency (discreteness) limited only by technical potentialities of the instruments employed. In this case, the accuracy and reliability of monitoring of the drilling mud properties depends upon the frequency of measurement of the aforementioned parameters. This permits continuous monitoring of the drilling mud properties and, in the long run, contributes to improving the quality of drilling mud as a whole.

The method of the invention is realized by the aforedescribed apparatus.

Figure 2:
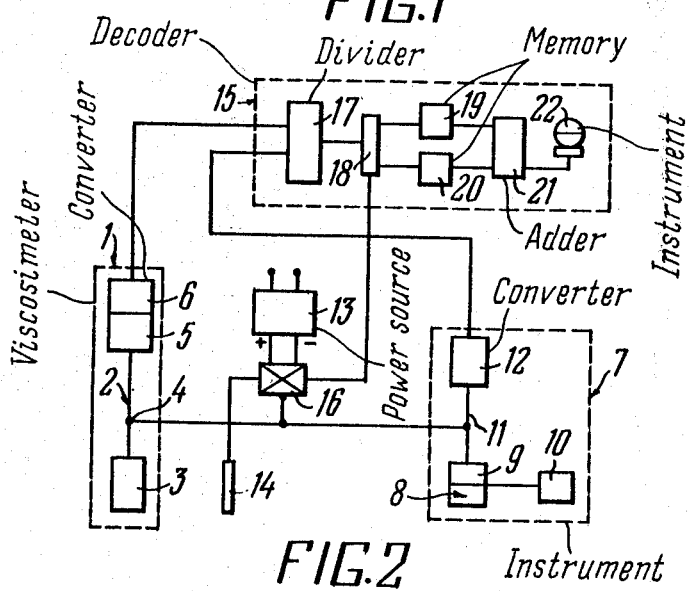
FIG. 2 is a block diagram of the embodiment of FIG. 1, including a block diagram of the decoder.

FIG. 2 is a block diagram of the apparatus of the invention for monitoring structural and mechanical properties of drilling mud. Similar elements in FIGS. 1 and 2 are numbered similarly.

As hereinbefore mentioned, the apparatus comprises a viscosimeter 1 having a driven sensitive element 2. An instrument 7 measures the shear strength and has a a driven sensitive element 8 immersed in the drilling mud. The viscosimeter 1 and the instrument 7 are provided with signal converters 6 and 12 which transform the signals fed from the sensitive elements 2 and 8, respectively, into signals characterizing the viscosity and shear strength of the drilling mud.

In principle, the presence of a converter depends upon the nature of signals obtained from the sensitive elements 2 and 8. If these signals are suitable for transmission to the decoder 15, the converters 6 and 12 may be mere amplifiers of said signals. The purpose of the converters is to shape signals fit for the decoder 15.

The decoder 15 is a logical circuit comprising a divider 17 for dividing the signals fed from the sensitive elements 2 and 8 or, likewise, from the converters 6 and 12.

The divider 17 has two inputs connected to the outputs of the converters 6 and 12, respectively. The output of the divider 17 is connected to a channel switch 18. The channel switch 18 is also coupled to the polarity reversal switch 16. The polarity reversal switch 16 is a conventional switch for connecting the poles of the power source 13 to the electrode 14 and the sensitive elements 2 and 8 in such a manner that, when positive potential is applied to said electrode, said sensitive elements have a negative potential, and vice versa. Practically, this connection is realized so that the shafts 4 and 11 of the sensitive elements 2 and 8, respectively, are connected via the polarity reversal switch 16 to one pole of the power source 13 and the electrode 14 is connected to the other pole of said power source. The channel switch 18 has two outputs. One of the outputs of the channel switch 18 is connected to a memory 19 and the other to a memory 20. Signals are distributed to the memories 19 and 20 in accordance with the signal supplied from the polarity reversal switch 16 to the channel switch 18. The outputs of the memories 19 and 20 are connected to an adder 21 which adds the signals and feeds the result to a recording instrument 22 which can be any output device. The instrument 22 produces the final result which is the ratio of the shear strength to the viscosity of the drilling mud. Such ratio is the aforementioned coagulation index.

The apparatus operates as follows. The motor 5 is turned on to rotate the blade 3, in order to measure the viscosity of the drilling mud. As the blade 3 rotates in the drilling mud, it overcomes the resistance proportional to the viscosity of the mud. Current in the circuit of the motor 5 grows proportional to the resistance to the rotation of the blade 3. The current signal is delivered to the divider 17. The signal from the sensitive element 2 can be of any nature (whether effort or torque) and it is transformed by the converter 6 into an electric signal which is also fed to the divider 17.

The motor 10 is turned on at the same time to measure the shear strength of the drilling mud and sets the sensitive element 8 into rotation. The sensitive element 8 is a sleeve filled with the drilling mud. The ribbed cylinder 9 is arranged therein. The motor 10 rotates the sleeve with the drilling mud, which starts rotating the cylinder 9 due to friction forces. The steel wire 11 is attached to the cylinder 9. The shear strength is determined by the twist angle of the wire 11 and the torque signal is transformed in the converter 12 into an electric signal proportional to the shear strength. Such signal is supplied to the second input of the divider 17. Positive potential is applied to the sensitive elements 2 and 8 from the power source 13 and negative potential is applied to the electrode 14. Finely dispersed and negatively charged clay particles concentrate near the positive electrodes, which are the sensitive elements 2 and 8 in this case. It should be stressed that the presence of such particles in the drilling mud defines all basic properties of the mud, its value for industrial application, including the viscosity and shear strength.

Growing concentration of the solid phase near the positive electrodes, that is, at the blade 3 and the cylinder 9, adds to the resistance to their rotation and consequently increases the current in the circuit of the motor 5 and proportionally increases the current of the signal, for example, in the converter 12.

In this manner, the divider 17 is fed signals from the converter 6 which are proportional to the maximum viscosity of the drilling mud, and signals from the converter 12 which are proportional to the maximum shear strength. The value of the signal proportional to the shear strength is divided by the value of the signal proportional to the viscosity of the drilling mud in the divider 17. The result of the first signal ratio is fed to the memory 19 via the channel switch 18. The polarity of the power source is then reversed to the sensitive elements 2 and 8 and the electrode 14 via the polarity reversal switch 16, either manually or automatically. Negative potential is applied to the sensitive elements 2 and 8, that is, they are connected to the negative pole (−) of the DC source 13, and the electrode 14 is connected to the positive pole of said DC source.

At the moment of polarity reversal of the sensitive elements 2 and 8 and the electrode 14, the switch 16 sends a command signal to the channel switch 18 to connect the output of the divider 17 to the input of the memory 20. When the polarity is reversed, the negatively charged particles concentrate in the zone of the electrode 14 and partially adhere thereto, thus leaving the zone of the sensitive elements 2 and 8 connected to the negative pole of the DC power source 13. This results in some reduction of viscosity and shear strength of the drilling mud in the zones of the sensitive elements 2 and 8 and, consequently, in some reduction of signals fed to the decoder 15 from the converters 6 and 12. The signals proportional to the viscosity and shear strength are delivered to the input of the divider 17 where the value of the signal proportional to the shear strength is divided by the value of the signal proportional to the viscosity of the drilling mud. The second ratio thus obtained is then supplied to the memory 20 via the channel switch 18.

At the moment, that the second ratio comes to the memory 20, the first ratio from the memory 19 and the second ratio from the memory 20 are supplied together to the adder 21 where the ratios are summed up and divided by two. Thus an arithmetical mean of the first and second ratios of the signals proportional to the shear strength and viscosity is obtained. The arithmetical mean value can be obtained differently, from division by two of the summed ratios in the adder 21, for example, by appropriate calibration of the recorder 22.

The coagulation index is an indication of the state and stability of the drilling mud and, consequently, is one of the basic parameters thereof. It is at present measured only in laboratories employing a great number of complicated instruments.

The invention has great industrial applicability, since it permits higher stability and quality of drilling muds, lower expenses for chemical agents (5–7%), control of adsorption and chemical activity of the solid phase in the drilling mud, lower expenses for regeneration of mud parameters and properties in the process of circulation (3–4%) and automation of the coagulation index measuring process.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of monitoring structural and mechanical properties of drilling mud, said method utilizing a power source having a pair of poles of opposite polarity and an electrode, said method including the steps of
   determining the viscosity of drilling mud by using a viscosimeter having a driven sensitive element,
   determining the shear strength of the drilling mud by using a shear strength measuring instrument having a driven sensitive element,
   immersing the driven sensitive elements into the drilling mud, and
   obtaining and comparing the data characteristics of the parameters measured, said method comprising the steps of
   connecting said sensitive elements to the same pole of said power source;
   connecting said electrode to the opposite pole of said power source and immersing said electrode in said drilling mud;
   measuring current flowing between said electrode and said sensitive elements, thereby obtaining electrical signals proportional to the viscosity and shear strength of said drilling mud upon stabilization of said current;
   determining a first ratio of said shear strength and viscosity signals;
   reversing the polarity of the poles of said power source;
   determining a second ratio of said shear strength and viscosity signals; and
   determining the arithmetical mean of said first and second ratios.

2. Apparatus for monitoring structural and mechanical properties of drilling mud, said apparatus including
   a viscosimeter having a driven sensitive element immersed in drilling mud,
   a shear strength measuring instrument having a driven sensitive element immersed in drilling mud,
   a first signal converter for converting signals from said sensitive element of said viscosimeter into signals indicating the viscosity of said drilling mud, said first signal converter having an input electrically connected to said sensitive element of said viscosimeter and an output, and
   a second signal converter for converting signals from said sensitive element of said shear strength measuring instrument into signals indicating the shear strength of said drilling mud, said second signal converter having an input electrically connected to said sensitive element of said shear strength measuring instrument and an output, said apparatus comprising
   a DC power source having a pair of poles of opposite polarity, one of said poles being electrically connected to said driven sensitive elements of said viscosimeter and said shear strength measuring instrument;
   an electrode immersed in said drilling mud and electrically connected to the other of said poles of said power source; and
   a divider having a pair of inputs electrically connected to the outputs of said first and second signal converters, respectively, and having an output and providing at said output signals indicating the ratio between the shear strength and viscosity of said drilling mud.

3. Apparatus as claimed in claim 2, further comprising
   a power source polarity reversal switch, said electrode being electrically connected to said other of said poles of said power source via said polarity reversal switch;
   a channel switch having a first input electrically connected to said polarity reversal switch, a second input electrically connected to the output of said divider and first and second outputs;
   a first memory having an input electrically connected to the first output of said channel switch and an output;
   a second memory having an input electrically connected to said second output of said channel switch and an output, said first and second memories forming first and second channels for the transmission and storage of information provided by said divider depending upon the position of said polarity reversal switch;
   an adder having first and second inputs electrically connected to the outputs of said first and second memories, respectively, and an output; and
   a data output device electrically connected to the output of said adder for providing the sum of the data obtained via said channels.

* * * * *